United States Patent
Nilsson et al.

(10) Patent No.: US 11,041,125 B2
(45) Date of Patent: Jun. 22, 2021

(54) DERIVATIZING OF THERMOCHEMICAL OIL

(71) Applicant: PREEM AKTIEBOLAG, Stockholm (SE)

(72) Inventors: Anders Nilsson, Järna (SE); Tomasz Janosik, Huddinge (SE); Tobias Ankner, Bandhagen (SE)

(73) Assignee: PREEM AKTIEBOLAG, Stockholm (SE)

( * ) Notice: Subject to any disclaimer, the term of this patent is extended or adjusted under 35 U.S.C. 154(b) by 0 days.

(21) Appl. No.: 16/768,470

(22) PCT Filed: Dec. 5, 2018

(86) PCT No.: PCT/EP2018/083637
§ 371 (c)(1),
(2) Date: May 29, 2020

(87) PCT Pub. No.: WO2019/110656
PCT Pub. Date: Jun. 13, 2019

(65) Prior Publication Data
US 2020/0385639 A1    Dec. 10, 2020

(30) Foreign Application Priority Data
Dec. 7, 2017 (EP) .................... 17205896

(51) Int. Cl.
| | |
|---|---|
| *C10G 3/00* | (2006.01) |
| *C07C 67/08* | (2006.01) |
| *C07C 67/03* | (2006.01) |
| *C10L 1/02* | (2006.01) |
| *C07C 67/54* | (2006.01) |
| *C10L 1/04* | (2006.01) |
| *C07C 67/02* | (2006.01) |

(52) U.S. Cl.
CPC .............. *C10G 3/50* (2013.01); *C07C 67/03* (2013.01); *C07C 67/08* (2013.01); *C07C 67/54* (2013.01); *C10L 1/02* (2013.01); *C10L 1/04* (2013.01); *C07C 67/02* (2013.01); *C10L 2200/0484* (2013.01); *C10L 2270/023* (2013.01); *C10L 2270/026* (2013.01); *C10L 2270/04* (2013.01)

(58) Field of Classification Search
CPC ........... C10G 3/50; C07C 67/08; C07C 67/54; C07C 67/02; C07C 67/0308; C10L 1/04; C10L 1/02
See application file for complete search history.

(56) References Cited

U.S. PATENT DOCUMENTS

| | | | |
|---|---|---|---|
| 2010/0152478 A1* | 6/2010 | Kiviranta ................. | C09F 1/04 560/129 |
| 2015/0210931 A1* | 7/2015 | Malyala .................... | C10G 3/48 585/240 |

FOREIGN PATENT DOCUMENTS

| | | |
|---|---|---|
| EP | 2774969 A1 | 9/2014 |
| WO | WO 2012/018524 A2 | 2/2012 |
| WO | WO 2015/006269 A1 | 1/2015 |

OTHER PUBLICATIONS

Lohitharn, N., et al., Upgrading of bio-oil: Effect of light aldehydes on acetic acid removal via esterification, Catalysis Communications, vol. 11, issue 2, pp. 96-99 (Year: 2009).*
Milina, M., et al., Prospectives for bio-oil upgrading via esterification over zeolite catalyst, Catalysis Today, vol. 234, pp. 176-183 (Year: 2014).*
Ciddor et al., "Catalytic upgrading of bio-oils by esterification", J Chem Technol Biotechnol, 2015, 90: 780-795.
Lohitharn et al, "Upgrading of bio-oil: Effect of light aldehydes on acetic acid removal via esterification", Catalysis Communications, 2009, 11: 96-99.
Milina et al., "Prospectives for bio-oil upgrading via esterification over zeolite catalysts", Catalysis Today, 2014, 235: 176-183.
Sundqvist et al., "Upgrading Fast Pyrolysis Bio-Oil Quality by Esterification and Azeotropic Water Removal", Energy Fuels, 2015, 29: 2527-2534.
Tanneru et al., "Pretreatment of bio-oil followed by upgrading via esterification to boiler fuel", Energy, 2014, 73: 214-220.
Zhang et al., "Catalytic upgrading of bio-oil using 1-octene a d 1-butanol over sulfonic acid resin catalysts", Green chemistry, 2011, 13: 940-949.
Zhang et al., "Catalytic Conversion of Bio-Oil to Oxygen-Containing Fuels by Acid-Catalyzed Reaction with Olefins and Alcohols over Silica Sulfuric Acid", Energies, 2013, 6: 4531-4550.

* cited by examiner

*Primary Examiner* — Yate' K Cutliff
(74) *Attorney, Agent, or Firm* — James S. Keddie; Bozicevic, Field & Francis LLP

(57) ABSTRACT

A process for obtaining an oil derivative. The process comprises the following steps: providing a thermochemical oil comprising a compound having a hydroxyl group, wherein the thermochemical oil is crude or refined oil resulting from thermochemical conversion of organic material; additionally providing a compound having an acyl group by feeding the compound having an acyl group, or a carboxylic acid or an ester as starting material for conversion to the compound having an acyl group, to the thermochemical oil; and reacting the compound having a hydroxyl group with the compound having an acyl group, thereby forming an ester between said compounds. A process for obtaining an intermediate composition, the process comprising blending the oil derivative with a refinery feedstock. An oil derivative or an intermediate composition. A process for obtaining a fuel component, the process comprising hydrotreating or hydrocracking the oil derivative or intermediate composition. A process for obtaining a fuel composition, the process comprising blending the fuel component with another component of a refinery fuel component pool. A fuel component or a fuel composition.

18 Claims, No Drawings

DERIVATIZING OF THERMOCHEMICAL OIL

CROSS-REFERENCE TO RELATED APPLICATIONS

This application is a § 371 national phase of International Application No. PCT/EP2018/083637, filed on Dec. 5, 2018, which claims the benefit of European Patent Application No. 17205896.8, filed on Dec. 7, 2017, which applications are incorporated by reference herein.

TECHNICAL FIELD

The present application relates to a process for obtaining an oil derivative, the process comprising provision of a thermochemical oil, such as a pyrolysis oil or a hydrothermal liquefaction oil; to a process for obtaining an intermediate composition; to an oil derivative and an intermediate composition; to a process for obtaining a fuel component; to a process for obtaining a fuel composition; and to a fuel component and a fuel composition.

BACKGROUND ART

Pyrolysis oils obtained by pyrolysis of different types of biomass (lignocellulosic biomass for instance) display properties making them very poorly miscible or completely immiscible with fossil petroleum distillate fuel feedstocks like light gas oil (LGO), vacuum gas oil (VGO) etc., or for that matter with lipophilic renewable refinery feedstocks like fatty acids or triglycerides (fats). Co-feeding of pyrolysis oils into standard hydrotreatment/hydrocracking oil refinery reactors for the manufacture of transport fuels and chemicals having a lowered carbon footprint is therefore challenging. In fact, even pyrolysis oils which have been hydrodeoxygenated in separate catalytic hydrogenation steps before co-feeding with fossil and other renewable feedstocks present problems with coking and plugging of reactor systems due to the chemical compositions obtained. The poor miscibility with fossil fuel feedstocks and with lipophilic renewable refinery feedstocks like fatty acids or fats also leads to issues with precipitation of feed components during pumping, which may clog pipes of continuous flow reactor equipment used in full scale oil refinery production or in smaller scale.

It is thus desirable to facilitate manufacture of for instance transportation fuels from pyrolysis oils and other thermochemical oils, especially manufacture by co-processing in an oil refinery with other renewable and/or fossil feedstocks.

WO 2012/018524 A2 discloses that biomass-derived pyrolysis oil may be esterified in the presence of alcohol prior to deoxygenation. As a result of esterification, the carboxylic acids in the biomass-derived pyrolysis oil are converted into esters to thereby yield a low acid biomass-derived pyrolysis oil.

EP 2 774 969 A1 discloses that a feedstock comprising bio-oil selected from bio-oils, any fractions of bio-oils and any combinations thereof is subjected to azeotropic distillation with at least one alcohol to yield a liquid component, and subjecting the liquid component to alcoholysis whereby converted bio-oil is obtained.

Milina et al., in Catalysis Today 2014, 235, 176-183, assess the potential of zeolite catalysts for bio-oil upgrading via esterification between acetic acid and o-cresol.

Tanneru et al., in Energy 2014, 73, 214-220, disclose oxidative pretreatment of pyrolysis bio-oils followed by esterification with alcohol.

Sundqvist et al., in Energy Fuels 2015, 29, 2527-2534, disclose esterification of pyrolysis bio-oil with methanol or n-butanol.

SUMMARY OF THE INVENTION

An object of the invention is to improve the miscibility between thermochemical oils and lipophilic refinery feedstocks. This object of the invention, as well as other objects of the invention which should be apparent to a person skilled in the art after having studied the description below, are accomplished by a process for obtaining an oil derivative, the process comprising the following steps: providing a thermochemical oil comprising a compound having a hydroxyl group, wherein the thermochemical oil is crude or refined oil resulting from thermochemical conversion of organic material; additionally providing a compound having an acyl group by feeding the compound having an acyl group, or a carboxylic acid or an ester as starting material for conversion to the compound having an acyl group, to the thermochemical oil; and reacting the compound having a hydroxyl group with the compound having an acyl group, thereby forming an ester between said compounds.

The invention thus solves the problem of poor miscibility between thermochemical oils and fossil and other lipophilic oil refinery feedstocks by esterification of, e.g., alcohols and, depending on esterification method, phenols of the thermochemical oil with, e.g., added fatty acids, or by transesterification of, e.g., added triglycerides (fats) with, e.g., alcohols of the thermochemical oil. Esterification or transesterification of components of the thermochemical oil results in an oil derivative having a significantly increased lipophilicity. The obtained oil derivative displays suitable properties for successful hydrotreatment/hydrocracking to transport fuels in standard oil refinery reactor systems with or without mixing with fossil feed components.

Herein, the term "thermochemical oil" refers to crude or refined oil resulting from thermochemical conversion, i.e. chemical conversion at elevated temperature, of organic material, such as biomass, preferably lignocellulosic biomass, e.g. sawdust or lignocellulosic products or side-products from agriculture, or organic waste, e.g. food waste and/or fossil, or partly fossil, waste, such as disposed tyres or plastics. The thermochemical conversion typically results in liquefaction of the organic material. Herein, the term "organic material" refers to carbon-based renewable or fossil material. The thermochemical oil may be a thermochemical bio oil, the term "bio" indicating that it results from thermochemical conversion of renewable organic material.

The thermochemical oil may be a pyrolysis oil, preferably a pyrolysis bio oil, a hydrothermal liquefaction oil, preferably a hydrothermal liquefaction bio oil, or a blend thereof, more preferably a pyrolysis oil, most preferably a pyrolysis bio oil. Herein, the term "pyrolysis oil" refers to a crude or refined oil resulting from pyrolysis of organic material.

Pyrolysis is a thermochemical decomposition of organic material, such as sawdust or disposed tyres, at elevated temperature in the absence of oxygen. Pyrolysis may involve thermal pyrolysis, catalytic pyrolysis or hydrogen pyrolysis. Herein, the term "hydrothermal liquefaction oil" refers to a crude or refined oil resulting from hydrothermal liquefaction of organic material. Hydrothermal liquefaction is a thermochemical decomposition of wet organic material, typically biomass, preferably lignocellulosic biomass, algae or food waste, in supercritical water at high pressure.

Techniques for forming an ester by reacting the compound having a hydroxyl group with the compound having an acyl group are well known to a person skilled in the art. Examples of such techniques are provided below.

The compound having a hydroxyl group may be an alcohol or a phenol, preferably an alcohol, or a compound having both alcohol and phenol functionality. When the hydroxyl group is an alcohol, esters may conveniently form via several routes of esterification and trans-esterification, as exemplified in the detailed description below.

The compound having an acyl group may be a carboxylic acid, an ester or a carboxylic acid anhydride. The compound having an acyl group may alternatively be a carboxylic acid chloride. Carboxylic acids and esters are readily available as renewable feedstocks. Carboxylic acid anhydrides form esters with both alcohols and phenols. Carboxylic acid chlorides similarly form esters, however with simultaneous release of stoichiometric chloride.

The compound having an acyl group may be provided by conversion of a carboxylic acid or an ester to a carboxylic acid anhydride or a carboxylic acid chloride, preferably by conversion of a carboxylic acid to a carboxylic acid anhydride. Conversion of carboxylic acids or esters, which are readily available as renewable feedstocks, to carboxylic acid anhydrides or carboxylic acid chlorides allows for effective formation of esters with the compound having a hydroxyl group. Carboxylic acids or esters may be converted to carboxylic acid anhydrides or carboxylic acid chlorides by reaction with, e.g., acetic anhydride or acetyl chloride, respectively. Conversion may occur separately from or integrated with reaction of the compound having a hydroxyl group with the compound having an acyl group In practice, the compound having an acyl group or the starting material for conversion to such compound may be provided as a composition of carboxylic acids, esters, carboxylic acid anhydrides, and/or carboxylic acid chlorides.

Herein, the expression "additionally providing a compound having an acyl group" refers to feeding of the compound having an acyl group, or the composition in the form of which the compound having an acyl group is provided, to the thermochemical oil. Herein, the term "additionally" refers to feeding of a separate feedstock to the thermochemical oil.

The acyl group may have a straight or branched, saturated or unsaturated, preferably saturated, carbon chain with at least 2 carbons, such as 2 to 24 carbons, preferably at least 4 carbons, such as 4 to 18 carbons, more preferably 6 to 18 carbons. The acyl group having a saturated carbon chain, the ester formed consumes less hydrogen in subsequent hydrotreatment or hydrocracking thereof. The acyl group having at least 2 carbons, the ester formed has a marked lipophilicity. The acyl group having at least 4 carbons, the ester formed will, after, e.g., hydrotreatment thereof, be of value in a gasoline or diesel boiling point range fuel composition. The acyl group having 3 to 6 carbons, such as in volatile fatty acids, the ester formed may thus contribute towards lipophilicity and fuel value. The acyl group having no more than 18 carbon atoms, the ester formed will, after, e.g., hydrotreatment, be of value in a gasoline or diesel fuel composition without a need for cracking thereof.

The carboxylic acid, either as the compound having an acyl group or as starting material for conversion to such compound, may be a fatty acid. The carboxylic acid anhydride may be a fatty acid anhydride. The carboxylic acid chloride may be a fatty acid chloride. The ester, either as the compound having an acyl group or as starting material for conversion to such compound, may be a triglyceride or a fatty acid ester. Herein, also in regard of the fatty acid group(s) of a fatty acid anhydride, fatty acid chloride, triglyceride or fatty acid ester, the term "fatty acid" refers to volatile fatty acids, having 3 to 6 carbons, as well as to long-chain fatty acids, having more than 6 carbons and typically up to 20 or 24 carbons. A long-chain fatty acid is preferred, making pronounced contribution to lipophilicity and fuel value.

The carboxylic acid, either as the compound having an acyl group or as starting material for conversion to such compound, may be provided as renewable feedstock, preferably as raw tall diesel, tall oil fatty acids (TOFA), palm fatty acid distillate (PFAD), hydrolyzed vegetable oil, hydrolyzed animal fat, algae oil fatty acids or volatile fatty acids having 3 to 6 carbons, or a blend thereof. The ester, either as the compound having an acyl group or as starting material for conversion to such compound, may be provided as renewable feedstock, preferably as vegetable oil, such as rapeseed oil or technical corn oil, animal fat, marine oil, algae oil, used cooking oil or fatty acid methyl esters (FAME), or a blend thereof.

Thermochemical oils in general have a high water content, which should be removed prior to fossil feedstock co-processing in oil refineries. The thermochemical oil may be dried using techniques like (vacuum) distillation, membrane filtration, extraction with an organic solvent which is recycled by distillation after phase separation, freeze drying etc. Provided that the thermochemical oil is relatively thermally stable, vacuum or ambient pressure distillation is considered preferred on an industrial scale.

Drying of the oil derivative is optionally performed by methods like (vacuum) distillation or phase separation, with or without assistance of electro-coalescence [5, 6]. Alternatively, the amount of water present after esterification is so small that dilution with components added during subsequent blending with refinery feedstock is enough to obtain satisfactory low total water content for subsequent hydrotreatment or hydrocracking.

Water and/or volatile compounds may be thus removed, preferably by vacuum or ambient pressure distillation, from the thermochemical oil or the oil derivative before, during and/or after, preferably before and/or after, more preferably after, reacting the compound having a hydroxyl group with the compound having an acyl group. Removal before and/or after reaction allows reaction conditions to be set independently of removal conditions. Removal after reaction results in a residue that is more convenient to handle from a rheological point of view.

The objects of the invention are also accomplished by a process for obtaining an intermediate composition, the process comprising the following steps: obtaining an oil derivative by the above-described process; and blending the oil derivative with a refinery feedstock being more lipophilic than the thermochemical oil.

The lipophilicity of the oil derivative and the refinery feedstock, respectively, may be determined as the partition coefficient of the oil derivative and the refinery feedstock between water and 1-octanol.

The refinery feedstock may be a fossil feedstock, preferably light gas oil (LGO) or vacuum gas oil (VGO), or a renewable feedstock, preferably a renewable feedstock comprising fatty acids or triglycerides. A feed, e.g. for subsequent hydrotreatment or hydrocracking, may thus be produced, which is either a mixture of liquids with varying amounts of solid materials, which mixture altogether can be pumped, or a homogeneous liquid, preferably at temperatures in the range of 0-140° C.

Depending on amounts of trace elements and glycerol in the oil derivative obtained by the above-described process, it may be useful to wash the oil derivative or intermediate composition, e.g. using aqueous extraction, for instance by methodology similar to what is used to desalt petrochemical feedstocks in oil refineries, such as by counter-current aqueous extraction [5]. Washing can be performed either before or after blending the oil derivative with the refinery feedstock.

The objects of the invention are also accomplished by an oil derivative or an intermediate composition obtainable by the respective above-described process. The composition of the oil derivative or intermediate composition, respectively, in particular in view of the ester content, oxygen content and/or chain length distribution thereof, is different from the composition of conventional fossil and/or renewable oil derivatives or intermediate compositions.

The objects of the invention are also accomplished by a process for obtaining a fuel component, the process comprising the following steps: obtaining an oil derivative or an intermediate composition by the respective above-described process; and hydrotreating or hydrocracking the oil derivative or intermediate composition.

Herein, the term "hydrotreating" refers to a process in which hydrogen is used to remove hetero-atoms, such as S or O, from the feedstock, such as by hydrodesulfurization, hydrodeoxygenation or hydrodecarboxylation, and/or to saturate the feedstock.

Herein, the term "hydrocracking" refers to cracking of higher molecular weight hydrocarbons into lower molecular weight hydrocarbons in the presence of hydrogen. The feedstock may thus be saturated and any sulfur and nitrogen present in the feedstock may also be hydrogenated and subsequently removed.

A feed comprising the oil derivative or the intermediate composition may thus be subjected to hydrotreatment and/or hydrocracking using oil refinery type processes, in which conventional hydrotreatment and/or hydrocracking catalysts, such as sulfided catalysts of NiMoS type, RuS type or CoMoS type, optionally bound to suitable support materials like porous alumina (gamma-alumina, theta-alumina etc.), catalyze a more or less complete hydrodeoxygenation of the feed to mixtures of hydrocarbons [7]. Other types of catalysts (e g precious metal catalysts on carbon support, nickel on silica, alumina or mixed silica/alumina supports) may be used if other types of products are desired, like phenols, alcohols, carboxylic acids etc.

Conventional conditions for catalytic hydrotreatment/hydrocracking may be employed. In continuous flow mode, such conditions are exemplified by, but not limited to, reaction temperatures in the range of 100-400° C., total working pressures in the range of 1-200 bar and with liquid hourly space velocity (LHSV) values in the range of 0.1-2 $h^{-1}$. In batch mode, such conditions are exemplified by, but not limited to, temperatures and total pressures from 1 bar up to 250-300 bar may be used. Catalyst loadings may, as conventional, vary between 0.1-50% of the weight of the feed mixture. Obtained hydrocarbon mixtures can be fractionated, e.g. by distillation, to different types of transport fuels or fuel components, lubricants, solvents and chemicals.

The fuel component may be a gasoline, kerosene or diesel fuel component.

Coke-formation or other undesired side reactions, such as precipitation of polar components, are suppressed when hydrotreating or hydrocracking the oil derivative rather than the thermochemical oil.

The objects of the invention are also accomplished by a process for obtaining a fuel composition, the process comprising the following steps: obtaining a fuel component by the above-described process; and blending the fuel component with another component of a refinery fuel component pool.

The fuel composition may be a gasoline, kerosene or diesel fuel.

The objects of the invention are also accomplished by a fuel component or a fuel composition obtainable by the respective above-described process. Being obtained from a thermochemical oil, the composition of the fuel component or fuel composition, respectively, in particular in view of the molecular structure thereof, such as the composition of straight, branched and cyclic hydrocarbons, is different from the composition of conventional fuel components or fuel compositions.

Esterification Techniques

Techniques for forming an ester by reacting the compound having a hydroxyl group with the compound having an acyl group are exemplified by, but not limited to, the following.

Acid-catalyzed esterification of the thermochemical oil with fatty acids. Mainly aliphatic alcohols of the thermochemical oil are reacted with fatty acids in the presence of acidic catalysts [1] like sulfuric acid or other mineral acids, acidic polymer-bound ion exchange resins like Amberlyst 15 or Amberlyst 70, molecular sieves, metal oxides like zeolites and sulfated metal oxides. Reaction temperatures may be in the range from ambient temperature to up to 250-300° C. The reaction, which is an equilibrium reaction, is often driven forward by simultaneous removal of water by vacuum or ambient pressure distillation, using molecular sieves added or other methods. This esterification method provides a partially esterified thermochemical oil, in which, as mentioned above, mostly or exclusively the aliphatic alcohols are esterified in varying yields. The product mixture has a lower acidity and therefore a higher stability than the starting thermochemical oil.

Trans-esterification [2] of triglycerides (fats) with the thermochemical oil. Mainly aliphatic alcohols of the thermochemical oil are reacted with triglycerides (fats) or other esters of fatty acids in the presence of Brønsted acids like sulfuric acid or other mineral acids, acidic polymer-bound ion exchange resins like Amberlyst 15 or Amberlyst 70, molecular sieves, metal oxides like zeolites and sulfated metal oxides, Lewis acids like titanium tetraethoxide or iron(II) sulfate, or in the presence of bases like for instance sodium or potassium methoxide or ethoxide, sodium or potassium hydroxide, calcium oxide and magnesium oxide. Trans-esterification may also be performed under neutral conditions [2]. Reaction temperatures may be in the range from ambient temperature to up to 250-300° C. The reaction, which is an equilibrium reaction, is often driven forward by either simultaneous removal of the more low-boiling alcohol in the original ester (in this case glycerol) by vacuum or ambient pressure distillation, or by other methods. This esterification method provides a partially esterified pyrolysis oil, in which, as mentioned above, mostly or exclusively the aliphatic alcohols are esterified in varying yields. The product mixture has a lower acidity and therefore a higher stability than the starting thermochemical oil.

Esterification of pyrolysis oils with fatty acid-containing anhydrides. Reaction of the alcohols and phenols in the thermochemical oil with either mixed anhydrides between fatty acids and a different carboxylic acid [3], or with symmetrical anhydrides of fatty acids [3], give rise to both alcohol and phenol esters and can therefore lead to a substantially higher degree of esterification of the thermochemical oil than for instance the two techniques mentioned above. This type of reaction requires that there is first a formation of either mixed or symmetrical anhydrides of the fatty acids, which then react with alcohols and phenols of the thermochemical oil catalyzed by bases like pyridine, trialkylamines, N-methylimidazole etc. The relatively high degree of esterification obtained depending on how the reaction is run, gives a stable and highly lipophilic product mixture.

Esterification of pyrolysis oil with fatty acids using other methods. There are many other types of reactions than the ones described above which can be used to prepare carboxylic esters [4]. One economically reasonable alternative to the methods described above, which also displays a good atom economy is to make esters by reacting acid chlorides with alcohols.

The obtained ester mixtures have a varying content of fatty acid esters of the alcohols and phenols (and carboxylic acids) of the pyrolysis oils depending on the method used for esterification, but all have improved properties such as increased lipophilicity in comparison with the starting pyrolysis oil and improved thermal stability, facilitating further processing in an oil refinery.

EXAMPLES

Analyses

Hydroxyl numbers related to aliphatic alcohols (ROH), phenols (ArOH) and carboxylic acids (COOH) were determined by $^{31}P$—NMR. $^1H$—NMR was used to characterize relative amounts of aromatic, aliphatic, ether/alcohol, aldehyde, ketone, carboxylic acid and olefin functionalities of the obtained product mixtures.

Molecular weight distributions, i.e. number average molecular weight $M_n$, weight average molecular weight $M_w$ and size average molecular weight $M_z$ were determined by gel permeation chromatography.

Elemental analysis was used to determine content of carbon, hydrogen, nitrogen and sulfur. Elemental analysis was performed by Micro-analytisches Laboratorium Kolbe, Mülheim an der Ruhr, Germany. The oxygen content was calculated by difference.

Depending on which product samples, other analyses which are not shown here have been performed (e g trace element analyses).

Raw Materials

Wood oil characterization: Pyrolysis oil produced by fast pyrolysis of wood material and subsequent condensation of the vapors was obtained from BTG Biomass Technology Group BV, Netherlands. Water content was determined by Karl Fisher titration and found to be 21% w/w. For further analytical characterization, a wood oil sample was dried over $MgSO_4$ after dilution in 10 volumes of ethyl acetate. After filtration and evaporation, the remaining sample weight was 60% of the input weight of wood oil. Hydroxyl numbers (Table 1) and molecular weight distributions (Table 2) were determined. $^1H$-NMR data are listed in Table 5. The interpretation of the weight reduction observed during dried wood oil sample preparation is that together with the water another 19% w/w of small, volatile components from the wood oil were adsorbed on the drying agent or removed during the solvent evaporation. More volatile components are not expected to contribute to the final biodiesel after hydrotreatment, as their carbon chain length are likely between one and four carbons only. The distillate from the derivatization below was analyzed with GC-MS, confirming acetic acid and acetic anhydride as major components.

Raw tall diesel characterization: Tall oil is a by-product from the pulp and paper industry and mainly consists of resin acids and free fatty acids. Raw tall diesel (RTD) is produced from tall oil through a (vacuum) distillation process, during which the content of free fatty acids is increased relative to the resin acids and other components. Raw tall diesel was obtained from Sunpine AB, Sweden. Hydroxyl numbers (Table 1) and molecular weight distributions (Table 2) were determined.

Rapeseed oil characterization: Rapeseed oil is a source of triglycerides and is assumed to contain negligible amounts of free hydroxyl groups. Molecular weight distributions were determined (Table 2).

TABLE 1

Hydroxyl numbers for raw materials

| Raw material | ROH (mmol/g) | ArOH (mmol/g) | COOH (mmol/g) |
|---|---|---|---|
| Wood oil | 3.0 | 2.5 | 0.4 |
| RTD | 0.04 | 0.05 | 3.75 |

TABLE 2

Molecular weight distributions for raw materials

| Raw material | $M_n$ | $M_w$ | $M_z$ |
|---|---|---|---|
| Wood oil | 269 | 467 | 916 |
| RTD | 337 | 367 | 392 |
| Rapeseed oil | 1344 | 1469 | 2025 |

Oil Derivatization

Example 1

Anhydride method: Wood oil (50.1 g) and RTD (124.5 g) were mixed at room temperature (rt). The mixture was pretreated by distilling off water and low boiling components (end conditions: 25 mbar/130° C.). A substantial amount of the mixture solidified. Acetic anhydride (32.4 g, ~2 equiv.) and N-methyl imidazole (NMI) (2.6 g, 0.2 equiv) were added and the resulting mixture was heated to 170° C. The temperature was decreased to 130° C. before distillation recommenced (end conditions: 30 mbar/150° C.). The product mixture obtained was in the form of a homogeneous dark syrup. Hydroxyl numbers were determined for the product oil (Table 3). The results correlate with a 93% derivatization of the alcohol functionalities. Molecular weight distributions were determined (Table 4). The results indicate a molecular weight distribution increase from $M_w$ 467 (wood oil) to $M_w$ 1502 for the product mixture. $^1H$-NMR-data are listed in Table 5 below. Elemental analysis data are shown in Table 6. The product mixture was subsequently blended with LGO (ratio 1:9, 1:4 or 3:7), providing homogeneous feeds suitable for hydrotreatment.

Example 2

The anhydride method described in Example 1 was used to prepare a derivatized wood oil mixture, using RTD as the carboxylic acid component. Upon completed esterification, the product mixture (61 g) was kept at 110° C. Hydroxyl numbers are shown in Table 3 and elemental analysis data are shown in Table 6. Further, RTD (61 g) and LGO (62 g) were charged to the product mixture to reach a ratio of derivatized wood oil/RTD/LGO of 1:1:1. This provided a homogeneous mixture, which was stable after cooling to ambient temperature. The resulting mixture is suitable as a feed for hydrotreatment.

Example 3

Wood oil (12.4 g) and oleic acid (44 g) were mixed at room temperature. The mixture was pretreated by distilling off water and low boiling components under reduced pressure (end conditions 130° C.). A substantial amount of the mixture solidified. Acetic anhydride (7.5 g) and N-methyl imidazole (NMI) (0.62 g) were added at 120° C. The resulting mixture was heated to 170° C. and was then kept at 170° C. for 20 min. The temperature was decreased to 110° C. before vacuum distillation recommenced at 110° C. The product mixture obtained was in the form of a homogeneous dark syrup. Hydroxyl numbers are shown in Table 3 and elemental analysis data are shown in Table 6. Additional oleic acid (22 g) was charged at 110° C., producing a homogeneous mixture, which was stable after cooling to ambient temperature. The resulting product mixture is suitable as feed for hydrotreatment.

Example 4

Fisher esterification: Wood oil (51.9 g) and RTD (100.6 g) were mixed at rt. The mixture was pretreated by distilling off water and low boiling components (end conditions: 22 mbar/130° C.). The temperature was lowered to 70° C. before sulfuric acid (98% w/w, 0.5 mL) was added and distillation recommenced (end conditions: 20-30 mbar/130° C.) for removal of water. The product consisted of a two phase mixture: a solid phase of 13 g and a liquid phase of 120 g. The hydroxyl numbers were determined separately for the two phases, and are also presented as a weighted result representing the product as a whole (Table 3). The results correlate with a 43% derivatization of the alcohol functionalities. Molecular weight distributions were determined separately for the two phases (Table 4). The results verify a molecular size increase from $M_w$ 467 (wood oil) to $M_w$ 2288 for the solid fraction and $M_w$ 725 for the liquid fraction. Solid phase and liquid phase were sampled for elemental and trace analysis (see Table 6). Representative samples of solid and liquid fractions were withdrawn (ratio solid fraction to liquid fraction 1:9. total weight 6.0 g), and incorporated into LGO (24 g) to provide a feed suitable for hydrotreatment.

Example 5

Acid catalyzed trans-esterification: Wood oil (51.7 g) and rapeseed oil (98.7 g) were mixed at rt. The mixture was pretreated by distilling off water and low boiling components (end conditions: 24 mbar/142° C.). The temperature was lowered to 100° C. before sulfuric acid (98% w/w, 0.1 mL) was added and distillation recommenced (end conditions: 22 mbar/142° C.) for 17 h to remove volatile components released during the reaction. The product consisted of a two phase mixture: a solid phase of 30 g and a liquid phase of 97 g. The hydroxyl numbers were determined separately for the two phases and are also presented as a weighted result representing the product as a whole (Table 3). The results correlate with a 43% derivatization of the alcohol functionalities. Molecular weight distributions were determined separately for the two phases (table 4). The results verify a molecular size increase from $M_w$ 467 (wood oil) to $M_w$ 2332 for the solid fraction and $M_w$ 1464 for the liquid fraction. Solid phase and liquid phase were sampled for elemental and trace analysis (Table 6). Representative samples of solid and liquid fractions were withdrawn (ratio solid fraction to liquid fraction 1:3.2, total weight 6.0 g), and incorporated into LGO (24 g) to provide a feed suitable for hydrotreatment.

TABLE 3

Hydroxyl numbers for oil derivatives

| Material | ROH (mmol/g) | ArOH (mmol/g) | COOH (mmol/g) |
|---|---|---|---|
| Example 1 | 0.06 | 0.02 | 1.7 |
| Example 2 | 0 | 0.02 | 4.02 |
| Example 3 | 0 | 0.03 | 9.16 |
| Example 4 Liquid | 0.16 | 0.49 | 2.43 |
| Example 4 Solid | 0.48 | 1.39 | 1.30 |
| Example 4 Weighted | 0.19 | 0.58 | 2.32 |
| Example 5 Liquid | 0.12 | 0.23 | 0.07 |
| Example 5 Solid | 0.82 | 1.27 | 0.14 |
| Example 5 Weighted | 0.29 | 0.49 | 0.09 |

TABLE 4

Molecular weight distributions for oil derivatives

| Material | $M_n$ | $M_w$ | $M_z$ |
|---|---|---|---|
| Example 1 | 473 | 1502 | 6584 |
| Example 4 Liquid | 384 | 725 | 3304 |
| Example 4 Solid | 612 | 2288 | 7472 |
| Example 5 Liquid | 613 | 1464 | 2585 |
| Example 5 Solid | 796 | 2332 | 6932 |

TABLE 5

$^1$H-NMR (CDCl$_3$) results for wood oil and for Examples 1-3 (normalized integrals)

| | ppm | Integral |
|---|---|---|
| Wood oil: $^1$H-NMR signals | | |
| Carboxylic acid H (COO$\underline{H}$) and aldehyde H (C$\underline{H}$O) | 12-9 | 3.10 |
| Aromatic H | 9-6.2 | 11.82 |
| Olefin H | 6.2-4.5 | 12.74 |
| Alifatic alcohol H, —C$\underline{H}$OH or alifatic ether —C$\underline{H}$OR | 4.5-3.3 | 23.53 |
| Alifatic H | 3.3-0 | 48.82 |
| Example 1: $^1$H-NMR signals | | |
| Carboxylic acid H (COO$\underline{H}$) and aldehyde H (C$\underline{H}$O) | 12-9 | 0.10 |
| Aromatic H | 9-6.2 | 1.78 |
| Olefin H | 6.2-4.5 | 11.74 |
| Alifatic alcohol H, —C$\underline{H}$OH or alifatic ether —C$\underline{H}$OR | 4.5-3.3 | 2.26 |
| Alifatic H | 3.3-0 | 84.12 |
| Example 2: $^1$H-NMR signals | | |
| Carboxylic acid H (COO$\underline{H}$) and aldehyde H (C$\underline{H}$O) | 12-9 | 0.02 |
| Aromatic H | 9-6.2 | 3.17 |
| Olefin H | 6.2-4.5 | 5.58 |

TABLE 5-continued $^1$H-NMR (CDCl$_3$) results for wood oil and for
Examples 1-3 (normalized integrals)

| | ppm | Integral |
|---|---|---|
| Alifatic alcohol H, —C<u>H</u>OH or alifatic ether —C<u>H</u>OR | 4.5-3.3 | 0.70 |
| Alifatic H | 3.3-0 | 90.53 |
| Example 3: $^1$H-NMR signals | | |
| Carboxylic acid H (COO<u>H</u>) and aldehyde H (C<u>H</u>O) | 12-9 | 0 |
| Aromatic H | 9-6.2 | 1.49 |
| Olefin H | 6.2-4.5 | 11.79 |
| Alifatic alcohol H, —C<u>H</u>OH or alifatic ether —C<u>H</u>OR | 4.5-3.3 | 1.16 |
| Alifatic H | 3.3-0 | 85.57 |

TABLE 6

Elemental compositions of raw materials and oil derivatives

| Sample | % C | % H | % N | % S | % O | Comment/description |
|---|---|---|---|---|---|---|
| Wood oil as delivered | 52.98 | 7.06 | 1.37 | 0.17 | 38.42 | Wood oil as delivered |
| Example 1 Product | 75.48 | 10.59 | 1.11 | <0.01 | 12.82 | Homogeneous, RTD-esterified wood oil |
| Example 2 Product | 76.40 | 10.40 | 0.64 | 0.06 | 12.5 | Homogeneous, RTD-esterified wood oil |
| Example 3 Product | 71.80 | 10.80 | 0.62 | 0.00 | 16.78 | Homogeneous, oleic acid-esterified wood oil |
| Example 4 Solid | 70.60 | 9.10 | 0.78 | 0.17 | 19.35 | Solid material 13 g from Fisher esterification |
| Example 4 Liquid | 76.10 | 10.66 | 0.96 | 0.25 | 12.03 | Oil 120 g from Fisher esterification |
| Example 4 Weighted | 75.56 | 10.50 | 0.94 | 0.24 | 12.75 | Combined material from Fisher esterification |
| Example 5 Solid | 69.00 | 8.49 | 0.18 | 0.34 | 21.99 | Solid material 30 g from acid catalyzed transesterification |
| Example 5 Liquid | 76.79 | 11.72 | 0.36 | <0.01 | 11.13 | Oil 97 g from acid catalyzed transesterification |
| Example 5 Weighted | 74.95 | 10.96 | 0.31 | 0.08 | 13.70 | Acid catalyzed transesterification |

REFERENCES

[1] M. B. Smith and J. March, Advanced Organic Chemistry, Reactions, Mechanisms and Structure, 6th Edition, John Wiley & Sons, 2007, ISBN 13: 978-0-471-72091-1, ISBN 10: 0-471-72091-7, pages 1414-1416 and references therein.

[2] M. B. Smith and J. March, Advanced Organic Chemistry, Reactions, Mechanisms and Structure, 6th Edition, John Wiley & Sons, 2007, ISBN 13: 978-0-471-72091-1, ISBN 10: 0-471-72091-7, pages 1419-1421 and references therein.

[3] M. B. Smith and J. March, Advanced Organic Chemistry, Reactions, Mechanisms and Structure, 6th Edition, John Wiley & Sons, 2007, ISBN 13: 978-0-471-72091-1, ISBN 10: 0-471-72091-7, pages 1412-1414 and references therein.

[4] Trost and Fleming, Comprehensive Organic Synthesis, Volume 6 Heteroatom Manipulation, Pergamon Press Ltd, 1991, Chapter 2.2 Synthesis of Esters, Activated Esters and Lactones, ISBN 0-08-040597-5, pages 323-380.

[5] a) µl-Otaibi et al., Energy Fuels 2005, 19, 2526 and in Perreira et al. "Crude Oil Desalting Process" http://dx-.doi.org/10.5772/61274.
b) U.S. Pat. No. 5,114,566.

[6] Mhatre et al., Chemical Engineering Research and Design 2015, 9, 177-195.

[7] Rinaldi et al., Catalytic Hydrogenation for Biomass Valorisation, ISBN 978-1-84973-801-9 and references therein.

ITEMIZED LIST OF EMBODIMENTS

1. A process for obtaining an oil derivative, the process comprising the following steps:
providing a thermochemical oil comprising a compound having a hydroxyl group;
additionally providing a compound having an acyl group; and
reacting the compound having a hydroxyl group with the compound having an acyl group, thereby forming an ester between said compounds.

2. The process according to item 1, wherein the thermochemical oil is a pyrolysis oil, preferably a pyrolysis bio oil, a hydrothermal liquefaction oil, preferably a hydrothermal liquefaction bio oil, or a blend thereof, more preferably a pyrolysis oil, most preferably a pyrolysis bio oil.

3. The process according to item 1 or 2, wherein the compound having a hydroxyl group is an alcohol or a phenol.

4. The process according to any one of the preceding items, wherein the compound having an acyl group is a carboxylic acid, an ester or a carboxylic acid anhydride.

5. The process according to any one of the preceding items, wherein the compound having an acyl group is provided by conversion of a carboxylic acid to a symmetrical or unsymmetrical carboxylic acid anhydride.

6. The process according to any one of the preceding items, wherein the acyl group has a straight or branched, saturated or unsaturated, preferably saturated, carbon chain with at least 2 carbons, such as 2 to 24 carbons, preferably at least 4 carbons, such as 4 to 18 carbons, more preferably 6 to 18 carbons.

7. The process according to any one of items 4 to 6, wherein the carboxylic acid or the carboxylic acid anhydride is a fatty acid or a fatty acid anhydride, respectively.

8. The process according to any one of items 4 to 7, wherein the ester is a triglyceride or a fatty acid ester.

9. The process according to any one of items 4 to 8, wherein the carboxylic acid is provided as renewable feedstock, preferably as raw tall diesel, tall oil fatty acids, palm fatty acid distillate, algae oil fatty acids or volatile fatty acids having 3 to 6 carbons, or a blend thereof; and/or the ester is provided as renewable feedstock, preferably as vegetable oil, such as rapeseed oil or technical corn oil, animal fat, marine oil, algae oil, used cooking oil or fatty acid methyl esters, or a blend thereof.

10. The process according to any one of the preceding items, wherein water and/or volatile compounds are removed, preferably by vacuum or ambient pressure distillation, from the thermochemical oil or the oil derivative before, during and/or after, preferably before and/or after, more preferably after, reacting the compound having a hydroxyl group with the compound having an acyl group.

11. A process for obtaining an intermediate composition, the process comprising the following steps: obtaining an oil derivative by the process according to any one of items 1 to 10; and blending the oil derivative with a refinery feedstock being more lipophilic than the thermochemical oil, such as a fossil feedstock, preferably light gas oil or vacuum gas oil, or a renewable feedstock, preferably a renewable feedstock comprising fatty acids or triglycerides.

12. An oil derivative obtainable by the process according to any one of items 1 to 10 or an intermediate composition obtainable by the process according to item 11.

13. A process for obtaining a fuel component, such as a gasoline, kerosene or diesel fuel component, the process comprising the following steps: obtaining an oil derivative by the process according to any one of items 1 to 10 or an intermediate composition by the process according to item 11; and hydrotreating or hydrocracking the oil derivative or intermediate composition.

14. A process for obtaining a fuel composition, such as a gasoline, kerosene or diesel fuel, the process comprising the following steps: obtaining a fuel component by the process according to item 13; and blending the fuel component with another component of a refinery fuel component pool.

15. A fuel component obtainable by the process according to item 13 or a fuel composition obtainable by the process according to item 14.

The invention claimed is:

1. A process for obtaining an oil derivative, the process comprising the following steps:
providing a thermochemical oil comprising a compound having a hydroxyl group, wherein the thermochemical oil is crude or refined oil resulting from thermochemical conversion of organic material;
additionally providing a compound having an acyl group by feeding the compound having an acyl group, or a carboxylic acid or an ester as starting material for conversion to the compound having an acyl group, to the thermochemical oil; and
reacting the compound having a hydroxyl group with the compound having an acyl group, thereby forming an ester between said compounds,
wherein the compound having a hydroxyl group is an alcohol or phenol.

2. The process according to claim 1, wherein the thermochemical oil is a pyrolysis oil, a hydrothermal liquefaction oil, or a blend thereof.

3. The process according to claim 1, wherein the compound having an acyl group is a carboxylic acid, an ester or a carboxylic acid anhydride.

4. The process according to claim 1, wherein the compound having an acyl group is provided by conversion of a carboxylic acid to a symmetrical or unsymmetrical carboxylic acid anhydride.

5. The process according to claim 1, wherein the acyl group has a straight or branched, saturated or unsaturated, carbon chain with at least 2 carbons.

6. The process according to claim 3, wherein the carboxylic acid or the carboxylic acid anhydride is a fatty acid or a fatty acid anhydride, respectively.

7. The process according to claim 3, wherein the ester is a triglyceride or a fatty acid ester.

8. The process according to claim 3, wherein the carboxylic acid is provided as renewable feedstock; and/or the ester is provided as renewable feedstock.

9. The process according to claim 1, wherein water and/or volatile compounds are removed from the thermochemical oil or the oil derivative before, during and/or after reacting the compound having a hydroxyl group with the compound having an acyl group.

10. A process for obtaining an intermediate composition, the process comprising the following steps:
obtaining an oil derivative by the process according to claim 1; and
blending the oil derivative with a refinery feedstock being more lipophilic than the thermochemical oil, or a renewable feedstock.

11. An oil derivative produced by the process according to claim 1, wherein the compound having an acyl group is a carboxylic acid or an ester and wherein the carboxylic acid is provided as renewable feedstock being raw tall diesel, tall oil fatty acids, palm fatty acid distillate, algae oil fatty acids or volatile fatty acids having 3 to 6 carbons, or a blend thereof; and/or the ester is provided as renewable feedstock being vegetable oil, animal fat, marine oil, algae oil, used cooking oil or fatty acid methyl esters, or a blend thereof.

12. A process for obtaining a fuel component, the process comprising the following steps:
obtaining an oil derivative by the process according to claim 1; and
hydrotreating or hydrocracking the oil derivative.

13. A process for obtaining a fuel composition, the process comprising the following steps:
obtaining a fuel component by the process according to claim 12; and
blending the fuel component with another component of a refinery fuel component pool.

14. A fuel component produced by the process according to claim 12, wherein the compound having an acyl group is a carboxylic acid or an ester and wherein the carboxylic acid is provided as renewable feedstock being raw tall diesel, tall oil fatty acids, palm fatty acid distillate, algae oil fatty acids or volatile fatty acids having 3 to 6 carbons, or a blend thereof; and/or the ester is provided as renewable feedstock being vegetable oil, animal fat, marine oil, algae oil, used cooking oil or fatty acid methyl esters, or a blend thereof.

15. An intermediate composition produced by the process according to claim 10, wherein the compound having an acyl group is a carboxylic acid or an ester and wherein the carboxylic acid is provided as renewable feedstock being raw tall diesel, tall oil fatty acids, palm fatty acid distillate, algae oil fatty acids or volatile fatty acids having 3 to 6 carbons, or a blend thereof; and/or the ester is provided as renewable feedstock being vegetable oil, animal fat, marine oil, algae oil, used cooking oil or fatty acid methyl esters, or a blend thereof.

16. A process for obtaining a fuel component, the process comprising the following steps:
obtaining an intermediate composition by the process according to claim 10; and
hydrotreating or hydrocracking the intermediate composition.

17. A fuel composition produce by the process of claim 13, wherein the compound having an acyl group is a carboxylic acid or an ester and wherein the carboxylic acid is provided as renewable feedstock being raw tall diesel, tall oil fatty acids, palm fatty acid distillate, algae oil fatty acids or volatile fatty acids having 3 to 6 carbons, or a blend thereof; and/or the ester is provided as renewable feedstock being vegetable oil, animal fat, marine oil, algae oil, used cooking oil or fatty acid methyl esters, or a blend thereof.

18. A fuel component produced by the process of claim 16, wherein the compound having an acyl group is a carboxylic acid or an ester and wherein the carboxylic acid is provided as renewable feedstock being raw tall diesel, tall oil fatty acids, palm fatty acid distillate, algae oil fatty acids or volatile fatty acids having 3 to 6 carbons, or a blend thereof; and/or the ester is provided as renewable feedstock being vegetable oil, animal fat, marine oil, algae oil, used cooking oil or fatty acid methyl esters, or a blend thereof.

* * * * *